US012773329B2

(12) United States Patent
Nordhausen et al.

(10) Patent No.: US 12,773,329 B2
(45) Date of Patent: Oct. 27, 2026

(54) METHODS AND SYSTEMS FOR FACILITATING LAMINAR FLOW BETWEEN CONDUITS

(71) Applicant: Merit Medical Systems, Inc., South Jordan, UT (US)

(72) Inventors: Craig Nordhausen, Salt Lake City, UT (US); John William Hall, Bountiful, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 854 days.

(21) Appl. No.: 18/175,419

(22) Filed: Feb. 27, 2023

(65) Prior Publication Data

US 2023/0310187 A1 Oct. 5, 2023

Related U.S. Application Data

(62) Division of application No. 15/875,194, filed on Jan. 19, 2018, now Pat. No. 11,590,010.

(Continued)

(51) Int. Cl.

*A61F 2/07* (2013.01)
*A61F 2/915* (2013.01)

(Continued)

(52) U.S. Cl.

CPC ................ *A61F 2/915* (2013.01); *A61F 2/07* (2013.01); *A61F 2/954* (2013.01); *A61F 2/958* (2013.01);

(Continued)

(58) Field of Classification Search

CPC ............ A61F 2/07; A61F 2/064; A61F 2/954; A61M 1/14; A61M 1/3655; A61M 1/3653; A61M 39/0247; A61M 39/04

See application file for complete search history.

(56) References Cited

U.S. PATENT DOCUMENTS 3,357,432 A 12/1967 Sparks
3,435,823 A 4/1969 Edwards (Continued)

FOREIGN PATENT DOCUMENTS

DE 4418910 12/1995
DE 29515546 3/1997

(Continued)

OTHER PUBLICATIONS

European Search Report dated Mar. 10, 2021 for EP18835705.7.

(Continued)

*Primary Examiner* — Brian A Dukert
(74) *Attorney, Agent, or Firm* — Dorsey & Whitney LLP

(57) ABSTRACT

Medical devices including vascular access kits and related system and methods are disclosed. In some embodiments, a vascular access system may include a first conduit, a second conduit, and an expandable stent that is coupled to both the first and second conduits such that there is a continuous lumen between the first conduit and the second conduit. Methods of deploying the vascular access system within the body of a mammal, more particularly, a human patient are disclosed. Methods of bypassing a section of vasculature of a mammal, more particularly, a human patient are disclosed. The vascular access system, when implanted and assembled, may be a fully subcutaneous surgical implant.

20 Claims, 10 Drawing Sheets

Related U.S. Application Data

(60) Provisional application No. 62/450,219, filed on Jan. 25, 2017.

(51) Int. Cl.
*A61F 2/954* (2013.01)
*A61F 2/958* (2013.01)
*A61M 25/10* (2013.01)
*A61F 2/97* (2013.01)

(52) U.S. Cl.
CPC ... *A61M 25/1018* (2013.01); *A61F 2002/075* (2013.01); *A61F 2002/91508* (2013.01); *A61F 2002/9583* (2013.01); *A61F 2/97* (2013.01); *A61F 2250/0039* (2013.01); *A61F 2250/006* (2013.01)

(56) References Cited

U.S. PATENT DOCUMENTS 3,490,438 A 1/1970 Lavender et al.
3,683,926 A 8/1972 Suzuki
3,814,137 A 6/1974 Martinez
3,818,511 A 6/1974 Goldberg et al.
3,826,257 A 7/1974 Buselmeier
3,853,126 A 12/1974 Schulte
3,882,862 A 5/1975 Berend
3,998,222 A 12/1976 Shihata
4,076,023 A 2/1978 Martinez
4,133,312 A 1/1979 Burd
4,184,489 A 1/1980 Burd
4,214,586 A 7/1980 Mericle
4,318,401 A 3/1982 Zimmernan
4,366,819 A 1/1983 Kaster
4,427,219 A 1/1984 Madej
4,441,215 A 4/1984 Kaster
4,447,237 A 5/1984 Frisch et al.
4,496,349 A 1/1985 Cosentino
4,496,350 A 1/1985 Cosentino
4,503,568 A 3/1985 Madras
4,550,447 A 11/1985 Seiler, Jr.
4,619,641 A 10/1986 Schanzer
4,655,771 A 4/1987 Wallersten
4,723,948 A 2/1988 Clark et al.
4,734,094 A 3/1988 Jacob et al.
4,753,236 A 6/1988 Healy
4,771,777 A 9/1988 Horzewski et al.
4,772,268 A 9/1988 Bates
4,786,345 A 11/1988 Wood
4,790,826 A 12/1988 Elftman
4,822,341 A 4/1989 Colone
4,848,343 A 7/1989 Wallsten et al.
4,850,999 A 7/1989 Planck
4,877,661 A 10/1989 House et al.
4,898,591 A 2/1990 Jang et al.
4,898,669 A 2/1990 Tesio
4,917,087 A 4/1990 Walsh et al.
4,919,127 A 4/1990 Pell
4,929,236 A 5/1990 Sampson
4,955,899 A 9/1990 Della Corna et al.
5,026,513 A 6/1991 House et al.
5,041,098 A 8/1991 Loiterman et al.
5,042,161 A 8/1991 Hodge
5,053,023 A 10/1991 Martin
5,061,275 A 10/1991 Wallsten et al.
5,061,276 A 10/1991 Tu et al.
5,064,435 A 11/1991 Porter
5,084,065 A 1/1992 Weldon et al.
5,104,402 A 4/1992 Melbin
5,171,227 A 12/1992 Twardowski et al.
5,171,305 A 12/1992 Schickling et al.
5,192,289 A 3/1993 Jessen
5,192,310 A 3/1993 Herweck et al.
5,197,976 A 3/1993 Herweck et al.
5,282,860 A 2/1994 Matsuno et al.
5,330,500 A 7/1994 Song
5,336,616 A 8/1994 Livesey et al.
5,399,168 A 3/1995 Wadsworth
5,405,320 A 4/1995 Twardowski et al.
5,405,339 A 4/1995 Kohnen et al.
5,454,790 A 10/1995 Dubrul
5,474,268 A 12/1995 Yu
5,474,563 A 12/1995 Myler et al.
5,476,451 A 12/1995 Ensminger et al.
5,496,294 A 3/1996 Hergenrother et al.
5,509,897 A 4/1996 Twardowski et al.
5,549,663 A 8/1996 Cottone, Jr.
5,558,641 A 9/1996 Glantz et al.
5,562,617 A 10/1996 Finch, Jr. et al.
5,562,618 A 10/1996 Cai et al.
5,591,226 A 1/1997 Trerotola et al.
5,607,463 A 3/1997 Schwartz et al.
5,624,413 A 4/1997 Markel et al.
5,637,088 A 6/1997 Wenner et al.
5,637,102 A 6/1997 Tolkoff et al.
5,645,532 A 7/1997 Horgan
5,647,855 A 7/1997 Trooskin
5,669,637 A 9/1997 Chitty et al.
5,669,881 A 9/1997 Dunshee
5,674,272 A 10/1997 Bush et al.
5,676,346 A 10/1997 Leinsing
5,743,894 A 4/1998 Swisher
5,755,773 A 5/1998 Schuster
5,755,775 A 5/1998 Trerotola et al.
5,792,104 A 8/1998 Speckman et al.
5,797,879 A 8/1998 Decampli
5,800,512 A 9/1998 Lentz et al.
5,800,514 A 9/1998 Nunez et al.
5,800,522 A 9/1998 Campbell
5,810,870 A 9/1998 Myers et al.
5,814,098 A 9/1998 Hinnenkamp et al.
5,830,224 A 11/1998 Cohn et al.
5,840,240 A 11/1998 Stenoien et al.
5,866,217 A 2/1999 Stenoien et al.
5,904,967 A 5/1999 Ezaki et al.
5,931,829 A 8/1999 Burbank et al.
5,931,865 A 8/1999 Silverman et al.
5,957,974 A 9/1999 Thompson et al.
5,997,562 A 12/1999 Zadno-Azizi
6,001,125 A 12/1999 Golds et al.
6,019,788 A 2/2000 Butters et al.
6,036,724 A 3/2000 Lentz et al.
6,102,884 A 8/2000 Squitieri
6,156,016 A 12/2000 Maginot
6,167,765 B1 1/2001 Weitzel
6,171,295 B1 1/2001 Garabedian
6,231,085 B1 5/2001 Olson
6,245,098 B1 6/2001 Feeser
6,261,255 B1 7/2001 Mullis et al.
6,261,257 B1 7/2001 Uflacker et al.
6,280,466 B1 8/2001 Kugler et al.
6,308,992 B1 10/2001 Mitsui et al.
6,309,411 B1 10/2001 Lashinski et al.
6,319,279 B1 11/2001 Shannon et al.
6,338,724 B1 1/2002 Dossa
6,398,764 B1 6/2002 Finch, Jr. et al.
6,402,767 B1 6/2002 Nash et al.
6,428,571 B1 8/2002 Lentz et al.
6,436,132 B1 8/2002 Patel et al.
6,582,409 B1 6/2003 Squitieri
6,585,762 B1 7/2003 Stanish
6,610,004 B2 8/2003 Viole et al.
6,689,096 B1 2/2004 Loubens et al.
6,689,157 B2 2/2004 Madrid et al.
6,692,461 B2 2/2004 Wantink
6,699,233 B2 3/2004 Slanda et al.
6,702,748 B1 3/2004 Nita et al.
6,702,781 B1 3/2004 Reifart et al.
6,706,025 B2 3/2004 Engelson et al.
6,719,781 B1 4/2004 Kim
6,719,783 B2 4/2004 Lentz et al.
6,730,096 B2 5/2004 Basta
6,733,459 B1 5/2004 Atsumi
6,740,273 B2 5/2004 Lee

(56) References Cited

U.S. PATENT DOCUMENTS 6,749,574 B2 6/2004 O'Keefe
6,752,826 B2 6/2004 Holloway et al.
6,758,836 B2 7/2004 Zawacki
6,858,019 B2 2/2005 Mcguckin, Jr. et al.
6,926,724 B1 8/2005 Chu
6,926,735 B2 8/2005 Henderson
6,976,952 B1 12/2005 Maini et al.
6,981,987 B2 1/2006 Huxel et al.
7,011,645 B2 3/2006 Mcguckin, Jr. et al.
7,025,741 B2 4/2006 Cull
7,044,937 B1 5/2006 Kirwan et al.
7,101,356 B2 9/2006 Miller
7,131,959 B2 11/2006 Blatter
7,211,074 B2 5/2007 Sansoucy
7,244,271 B2 7/2007 Lenz et al.
7,244,272 B2 7/2007 Dubson et al.
7,252,649 B2 8/2007 Sherry
7,297,158 B2 11/2007 Jensen
7,351,257 B2 4/2008 Kaldany
7,399,296 B2 7/2008 Poole et al.
7,438,699 B2 10/2008 Pecor et al.
7,452,374 B2 11/2008 Hain et al.
7,507,229 B2 3/2009 Hewitt et al.
7,588,551 B2 9/2009 Gertner
7,607,237 B2 10/2009 Schafer
7,708,722 B2 5/2010 Glenn
7,722,665 B2 5/2010 Anwar et al.
RE41,448 E 7/2010 Squitieri
7,762,977 B2 7/2010 Porter et al.
7,789,908 B2 9/2010 Sowinski et al.
7,828,833 B2 11/2010 Haverkost et al.
7,833,214 B2 11/2010 Wilson et al.
7,846,139 B2 12/2010 Zinn et al.
7,850,675 B2 12/2010 Bell et al.
7,850,705 B2 12/2010 Bachinski et al.
7,922,757 B2 4/2011 Mcguckin
D637,500 S 5/2011 Corbin
7,972,314 B2 7/2011 Bizup et al.
8,079,973 B2 * 12/2011 Herrig ................. A61M 1/3653 604/8
8,092,435 B2 1/2012 Beling et al.
8,313,524 B2 11/2012 Edwin et al.
8,388,634 B2 3/2013 Rubenstein et al.
8,512,312 B2 8/2013 Sage
8,551,139 B2 10/2013 Surti et al.
8,690,815 B2 4/2014 Porter et al.
8,776,387 B1 7/2014 Butler-Ammar
8,951,355 B2 2/2015 Boyle, Jr. et al.
9,278,172 B2 3/2016 Herrig et al.
9,517,124 B2 * 12/2016 Sithian ...................... A61F 2/07
9,642,623 B2 5/2017 Agarwal et al.
9,731,113 B2 8/2017 Grace et al.
10,172,673 B2 1/2019 Viswanathan et al.
2001/0011421 A1 8/2001 Bakke et al.
2001/0053930 A1 12/2001 Kugler et al.
2002/0049403 A1 * 4/2002 Alanis ....................... A61F 2/06 623/1.36
2002/0055766 A1 5/2002 Wallace et al.
2002/0055771 A1 5/2002 Sandock
2002/0099432 A1 7/2002 Yee
2002/0151761 A1 10/2002 Viole et al.
2003/0100859 A1 5/2003 Henderson et al.
2003/0125789 A1 7/2003 Ross et al.
2003/0135258 A1 7/2003 Andreas et al.
2003/0135261 A1 7/2003 Kugler et al.
2003/0139806 A1 7/2003 Haverkost et al.
2003/0181969 A1 9/2003 Kugler et al.
2003/0212385 A1 11/2003 Brenner et al.
2003/0212431 A1 11/2003 Brady et al.
2004/0024442 A1 2/2004 Sowinkski et al.
2004/0054405 A1 3/2004 Thierry et al.
2004/0073282 A1 4/2004 Stanish
2004/0078071 A1 4/2004 Escamilla et al.
2004/0147866 A1 7/2004 Blatter et al.
2004/0193242 A1 9/2004 Lentz et al.
2004/0215058 A1 10/2004 Zirps et al.
2004/0215337 A1 10/2004 Hain et al.
2004/0236412 A1 11/2004 Brar
2005/0004553 A1 1/2005 Douk
2005/0137614 A1 6/2005 Porter et al.
2005/0192559 A1 9/2005 Michels et al.
2005/0203457 A1 9/2005 Smego
2005/0209581 A1 9/2005 Butts et al.
2005/0215938 A1 9/2005 Khan et al.
2006/0004392 A1 1/2006 Amarant
2006/0029465 A1 2/2006 Auer
2006/0058867 A1 3/2006 Thistle et al.
2006/0064159 A1 3/2006 Porter et al.
2006/0081260 A1 4/2006 Eells et al.
2006/0118236 A1 6/2006 House et al.
2007/0038288 A1 2/2007 Lye et al.
2007/0078412 A1 4/2007 McGuckin, Jr. et al.
2007/0078416 A1 4/2007 Eliasen
2007/0078438 A1 4/2007 Okada
2007/0088336 A1 4/2007 Dalton
2007/0123811 A1 5/2007 Squitieri
2007/0135775 A1 6/2007 Edoga et al.
2007/0142850 A1 6/2007 Fowler
2007/0161958 A1 7/2007 Glenn
2007/0167901 A1 7/2007 Herrig et al.
2007/0168019 A1 7/2007 Amplatz et al.
2007/0173868 A1 7/2007 Bachinski et al.
2007/0191779 A1 8/2007 Shubayev et al.
2007/0197856 A1 8/2007 Gellman et al.
2007/0213838 A1 9/2007 Hengelmolen
2007/0219510 A1 9/2007 Zinn et al.
2007/0233018 A1 10/2007 Bizup et al.
2007/0244539 A1 10/2007 Lentz et al.
2007/0249986 A1 10/2007 Smego
2007/0249987 A1 10/2007 Gertner
2007/0265584 A1 11/2007 Hickman et al.
2007/0293823 A1 12/2007 Sherry
2007/0293829 A1 12/2007 Conlon et al.
2008/0009781 A1 1/2008 Anwar et al.
2008/0027534 A1 1/2008 Edwin et al.
2008/0132924 A1 6/2008 Mcguckin
2008/0167595 A1 7/2008 Porter et al.
2008/0221469 A1 9/2008 Shevchuk
2008/0306580 A1 12/2008 Jenson et al.
2009/0076587 A1 3/2009 Cully et al.
2009/0137944 A1 5/2009 Haarala et al.
2009/0179422 A1 7/2009 Werth
2009/0187158 A1 7/2009 Richmond
2009/0227932 A1 9/2009 Herrig
2009/0234267 A1 9/2009 Ross
2009/0318895 A1 12/2009 Lachner
2010/0154800 A1 6/2010 Chang et al.
2010/0160718 A1 6/2010 Villafana et al.
2010/0160847 A1 6/2010 Braido et al.
2010/0161040 A1 6/2010 Braido et al.
2010/0198079 A1 8/2010 Ross
2010/0268188 A1 10/2010 Hanson
2010/0268196 A1 10/2010 Hastings et al.
2010/0292774 A1 11/2010 Shalev
2011/0015723 A1 1/2011 Batiste et al.
2011/0054312 A1 3/2011 Bell et al.
2011/0060264 A1 3/2011 Porter et al.
2011/0112482 A1 5/2011 Redd
2011/0208218 A1 8/2011 Ball
2011/0257609 A1 10/2011 Bizup et al.
2011/0264080 A1 10/2011 Lim et al.
2011/0295181 A1 12/2011 Dann et al.
2012/0059305 A1 3/2012 Akingba
2012/0065652 A1 3/2012 Cully et al.
2012/0078202 A1 3/2012 Beling et al.
2013/0060268 A1 3/2013 Herrig
2013/0204275 A1 8/2013 Agarwal et al.
2013/0338559 A1 12/2013 Franano et al.
2014/0018721 A1 1/2014 Gage et al.
2014/0094841 A1 4/2014 Sutton et al.
2014/0155908 A1 6/2014 Rosenbluth et al.
2014/0276215 A1 9/2014 Nelson
2014/0288638 A1 9/2014 Knight et al.
2014/0371779 A1 12/2014 Vale et al.

(56) References Cited

U.S. PATENT DOCUMENTS

| | | | |
|---|---|---|---|
| 2015/0051532 | A1 | 2/2015 | Tomko et al. |
| 2015/0082604 | A1 | 3/2015 | Cully et al. |
| 2015/0094744 | A1 | 4/2015 | Aghayev et al. |
| 2015/0150640 | A1 | 6/2015 | Boyle et al. |
| 2015/0257775 | A1 | 9/2015 | Gilvarry et al. |
| 2015/0265393 | A1 | 9/2015 | Stonebridge et al. |
| 2016/0066954 | A1 | 3/2016 | Miller et al. |
| 2016/0129177 | A1 | 5/2016 | Herrig |
| 2016/0136398 | A1 | 5/2016 | Heilman et al. |
| 2016/0279317 | A1 | 9/2016 | Gale et al. |
| 2017/0020556 | A1 | 1/2017 | Sutton et al. |
| 2018/0271637 | A1 | 9/2018 | Hall et al. |
| 2019/0015627 | A1 | 1/2019 | Hall et al. |
| 2019/0022368 | A1 | 1/2019 | Hall et al. |
| 2019/0126017 | A1 | 5/2019 | Hall et al. |

FOREIGN PATENT DOCUMENTS

| | | |
|---|---|---|
| DE | 102008055587 | 8/2009 |
| EP | 1797831 | 6/2007 |
| JP | 62112567 | 5/1987 |
| JP | 04507050 | 12/1992 |
| JP | 05212107 | 8/1993 |
| JP | 06105798 | 4/1994 |
| JP | 09084871 | 3/1997 |
| JP | 09264468 | 7/1997 |
| JP | 2003501223 | 1/2003 |
| JP | 3995057 | 10/2007 |
| JP | 2008511414 | 4/2008 |
| KR | 101026933 | 4/2011 |
| KR | 20110036848 | 4/2011 |
| WO | 198403036 | 8/1984 |
| WO | 199008509 | 8/1990 |
| WO | 199519200 | 7/1995 |
| WO | 199624399 | 8/1996 |
| WO | 1998034676 | 8/1998 |
| WO | 2000027299 | 5/2000 |
| WO | 200076577 | 12/2000 |
| WO | 200105447 | 1/2001 |
| WO | 200105463 | 1/2001 |
| WO | 2001028456 | 4/2001 |
| WO | 2004032991 | 4/2004 |
| WO | 2004112880 | 12/2004 |
| WO | 2006026687 | 9/2006 |
| WO | 2009059371 | 5/2009 |
| WO | 2010059102 | 5/2010 |
| WO | 2011060386 | 5/2011 |
| WO | 2011153302 | 12/2011 |
| WO | 2015100251 | 7/2015 |

OTHER PUBLICATIONS

European Search Report dated Mar. 22, 2021 for EP18832124.4.
European Search Report dated Jun. 8, 2005 for EP05006233.0.
European Search Report dated Jul. 24, 2020 for EP18738538.0.
European Search Report dated Oct. 2, 2020 for EP18745239.6.
European Search Report dated Oct. 26, 2020 for EP18738538.0.
European Search Report dated Oct. 28, 2020 for EP18771028.0.
European Search Report dated Dec. 3, 2013 for EP05793066.1.
Office Action dated Apr. 28, 2020 for U.S. Appl. No. 14/192,567.
Office Action dated May 1, 2020 for U.S. Appl. No. 15/693,010.
Office Action dated May 5, 2010 for U.S. Appl. No. 10/962,200.
Office Action dated May 5, 2020 for U.S. Appl. No. 15/910,273.
Office Action dated May 21, 2021 for U.S. Appl. No. 15/826,977.
Office Action dated May 22, 2019 for U.S. Appl. No. 14/450,468.
Office Action dated May 24, 2018 for U.S. Appl. No. 14/995,270.
Office Action dated Jun. 3, 2021 for U.S. Appl. No. 16/039,943.
Office Action dated Jun. 4, 2018 for U.S. Appl. No. 14/192,567.
Office Action dated Jun. 9, 2016 for U.S. Appl. No. 14/192,567.
Office Action dated Jun. 15, 2017 for U.S. Appl. No. 14/192,567.
Office Action dated Jun. 15, 2021 for U.S. Appl. No. 15/934,152.
Office Action dated Jun. 17, 2019 for U.S. Appl. No. 15/035,626.
Office Action dated Jul. 11, 2018 for U.S. Appl. No. 14/450,468.
Office Action dated Jul. 19, 2018 for U.S. Appl. No. 15/035,626.
Office Action dated Jul. 23, 2019 for U.S. Appl. No. 14/332,091.
Office Action dated Aug. 5, 2020 for U.S. Appl. No. 15/875,194.
Office Action dated Aug. 7, 2017 for U.S. Appl. No. 14/450,468.
Office Action dated Aug. 12, 2010 for U.S. Appl. No. 10/962,200.
Office Action dated Aug. 15, 2016 for U.S. Appl. No. 14/332,091.
Office Action dated Aug. 18, 2020 for U.S. Appl No. 15/934,152.
Office Action dated Aug. 21, 2019 for U.S. Appl. No. 14/192,567.
Office Action dated Sep. 20, 2012 for U.S. Appl. No. 12/831,092.
Office Action dated Sep. 22, 2021 for U.S. Appl. No. 15/875,194.
Office Action dated Sep. 26, 2019 for U.S. Appl. No. 15/693,010.
Office Action dated Sep. 30, 2019 for U.S. Appl. No. 15/875,194.
Office Action dated Oct. 1, 2018 for U.S. Appl. No. 14/332,091.
Office Action dated Oct. 1, 2020 for U.S. Appl. No. 15/868,313.
Office Action dated Oct. 6, 2021 for U.S. Appl. No. 15/934,152.
Office Action dated Oct. 17, 2019 for U.S. Appl. No. 15/828,040.
Office Action dated Oct. 22, 2019 for U.S. Appl. No. 15/035,526.
Office Action dated Oct. 27, 2015 for U.S. Appl. No. 14/192,567.
Office Action dated Nov. 19, 2021 for U.S. Appl. No. 15/868,313.
Office Action dated Nov. 24, 2020 for U.S. Appl. No. 15/826,977.
Office Action dated Nov. 26, 2007 for U.S. Appl. No. 10/962,200.
Office Action dated Nov. 29, 2019 for U.S. Appl. No. 15/934,152.
Office Action dated Nov. 30, 2020 for U.S. Appl. No. 15/910,273.
Office Action dated Dec. 5, 2017 for U.S. Appl. No. 14/995,270.
Office Action dated Dec. 5, 2018 for U.S. Appl. No. 14/450,468.
Office Action dated Dec. 7, 2018 for U.S. Appl. No. 14/192,567.
Office Action dated Dec. 7, 2020 for U.S. Appl. No. 16/033,515.
Office Action dated Dec. 11, 2020 for U.S. Appl. No. 16/039,943.
European Search Report dated Dec. 4, 2020 for 18764826.6.
International Preliminary Report dated Mar. 12, 2014 for PCT/US2012/053967.
International Search Report and Written Opinion dated Jan. 18, 2019 for PCT/US2018/041821.
International Search Report and Written Opinion dated Jan. 28, 2015 for PCT/US2014/049547.
International Search Report and Written Opinion dated Mar. 15, 2013 for PCT/US2012/053967.
International Search Report and Written Opinion dated Mar. 16, 2015 for PCT/US2014/046630.
International Search Report and Written Opinion dated Apr. 4, 2019 for PCT/US2018/058179.
International Search Report and Written Opinion dated May 2, 2018 for PCT/US2018/013326.
International Search Report and Written Opinion dated May 3, 2013 for PCT/US2012/053967.
International Search Report and Written Opinion dated May 6, 1998 for PCT/US1998/001939.
International Search Report and Written Opinion dated Jun. 3, 2009 for PCT/US2009/035923.
International Search Report and Written Opinion dated Jun. 15, 2018 for PCT/US2018/020614.
International Search Report and Written Opinion dated Jun. 20, 2007 for PCT/US2006/044564.
International Search Report and Written Opinion dated Jul. 17, 2018 for PCT/US2018/023956.
International Search Report and Written Opinion dated Oct. 30, 2018 for PCT/US2018/042900.
International Search Report and Written Opinion dated Jun. 22, 2018 for PCT/US2018/014371.
Notice of Allowance dated Mar. 3, 2020 for U.S. Appl. No. 15/035,626.
Notice of Allowance dated Mar. 11, 2020 for U.S. Appl. No. 15/828,040.
Notice of Allowance dated Mar. 15, 2010 for U.S. Appl. No. 11/216,536.
Notice of Allowance dated Mar. 24, 2021 for U.S. Appl. No. 15/910,273.
Notice of Allowance dated Aug. 3, 2021 for U.S. Appl. No. 16/033,515.
Notice of Allowance dated Oct. 2, 2020 for U.S. Appl. No. 15/933,815.
Notice of Allowance dated Oct. 4, 2013 for U.S. Appl. No. 12/831,092.
Notice of Allowance dated Oct. 5, 2018 for U.S. Appl. No. 15/093,622.

(56) References Cited

OTHER PUBLICATIONS

Notice of Allowance dated Nov. 6, 2018 for U.S. Appl. No. 14/995,270.
Notice of Allowance dated Dec. 7, 2022 for U.S. Appl. No. 15/875,194.
Office Action dated Jan. 8, 2019 for U.S. Appl. No. 15/035,626.
Office Action dated Jan. 9, 2018 for U.S. Appl. No. 14/450,468.
Office Action dated Feb. 6, 2013 for U.S. Appl. No. 12/831,092.
Office Action dated Feb. 18, 2022 for U.S. Appl. No. 15/875,194.
Office Action dated Feb. 21, 2017 for U.S. Appl. No. 14/192,567.
Office Action dated Mar. 3, 2021 for U.S. Appl. No. 15/934,152.
Office Action dated Mar. 10, 2022 for U.S. Appl. No. 15/934,152.
Office Action dated Mar. 15, 2018 for U.S. Appl. No. 14/332,091.
Office Action dated Mar. 29, 2019 for U.S. Appl. No. 14/332,091.
Office Action dated Mar. 29, 2021 for U.S. Appl. No. 16/033,515.
Office Action dated Apr. 6, 2021 for U.S. Appl. No. 16/284,526.
Office Action dated Apr. 16, 2020 for U.S. Appl. No. 15/868,313.
Office Action dated Apr. 17, 2020 for U.S. Appl. No. 15/875,194.
Office Action dated Apr. 17, 2020 for U.S. Appl. No. 15/934,152.
Office Action dated Apr. 21, 2021 for U.S. Appl. No. 15/875,194.
Office Action dated Apr. 27, 2021 for U.S. Appl. No. 15/868,313.
Office Action dated Dec. 17, 2021 for U.S. Appl. No. 16/039,943.
Office Action dated Dec. 20, 2017 for U.S. Appl. No. 14/192,567.
Office Action dated Dec. 30, 2016 for U.S. Appl. No. 14/450,468.
"Clinical Reveiw of MTI, Onxy Liquid Embolization System", available at http://www.fda.gov/ohrms/dockets/ac/03/briefing/3975b1-02-clinical-review.pdf. accessed Aug. 29, 2005.
Besarab , et al., "Measuring the Adequacy of Hemodialysis Access", Current Opinion in Nephrology and Hypertension, Rapid Science Publishers ISSN, Jan. 1, 1996, 1062-4821.
Coulson MD , et al., "Modification of Venous End of Dialysis Grafts: An Attempt to Reduce Neointimal Hyperplasia", Dialysis & Transplantation, vol. 29 No. 1, Jan. 1, 2000, 10-18.
Coulson MD, Phd , et al., "A Combination of the Elephant Trunk Anastomosis Technique and Vascular Clips for Dialysis Grafts", Surgical Rounds, Nov. 1, 1999, 596-608.
Kanterman , et al., "Dialysis Access Grafts: Anatomic Location of Venous Stenosis and Results of Angioplasty", Interventional Radiology, vol. 195 No. 1, 195, Apr. 1, 1995, 135-139.
Kumpe , et al., "Angioplasty/Thrombolytic Treatment of Failing and Failed Hemodialysis Access Sites: Comparison with Surgical Treatment", Progress in Cardiovascular Diseases, vol. XXXIV No. 4, 1992, 263-278.
Lin , et al., "Contemporary Vascular Access Surgery for Chronic Haemodialysis", They Royal College of Surgeons of Edinburgh, J.R. Coll, Surg, Edinb., 41, Jun. 1, 1996, 164-169.
Peterson , et al., "Subclavian Venous Stenosis: A Complication of Subclavian Dialysis", The Journal of American Medical Association, vol. 252 No. 24, Dec. 28, 1994, 3404-3406.
Raju M.D. , "Techniques for Insertion and Management of Complications", PTFE Grafts for Hemodialysis Access, Ann. Surg., vol. 206 No. 5, Nov. 1, 1987, 666-673.
Sharafuddin , et al., "Percutaneous Balloon-Assisted Aspiration Thrombectomy of clotted ahemodialysis Access Grafts", Journal of Vascular and Interventional Radiology, vol. 7 No. 2, 1996, 177-183.
Notice of Allowance dated Mar. 31, 2022 for U.S. Appl. No. 15/868,313.
European Examination Report dated Aug. 25, 2023 for EP187385380.
European Search Report dated Jan. 23, 2025 for EP24189145.6.

* cited by examiner

METHODS AND SYSTEMS FOR FACILITATING LAMINAR FLOW BETWEEN CONDUITS

RELATED APPLICATIONS

This application is a Divisional of U.S. application Ser. No. 15/875,194, filed on Jan. 19, 2018 and titled "METHODS AND SYSTEMS FOR FACILITATING LAMINAR FLOW BETWEEN CONDUITS," which claims priority to U.S. Provisional Application No. 62/450,219, filed on Jan. 25, 2017 and titled "METHODS AND SYSTEMS FOR FACILITATING LAMINAR FLOW BETWEEN CONDUITS," which are both hereby incorporated by reference in their entireties.

TECHNICAL FIELD

The field of the present disclosure relates generally to medical devices. More specifically, the present disclosure relates to conduits, such as catheters and grafts, which are used to provide access into the body and methods and systems for coupling conduits. In some embodiments, the present disclosure relates to the selection and use of a stent to couple one or more conduits together.

BRIEF DESCRIPTION OF THE DRAWINGS

The embodiments disclosed herein will become more fully apparent from the following description and appended claims, taken in conjunction with the accompanying drawings. The drawings depict only typical embodiments, which embodiments will be described with additional specificity and detail in connection with the drawings in which:

DETAILED DESCRIPTION

Figure 1:
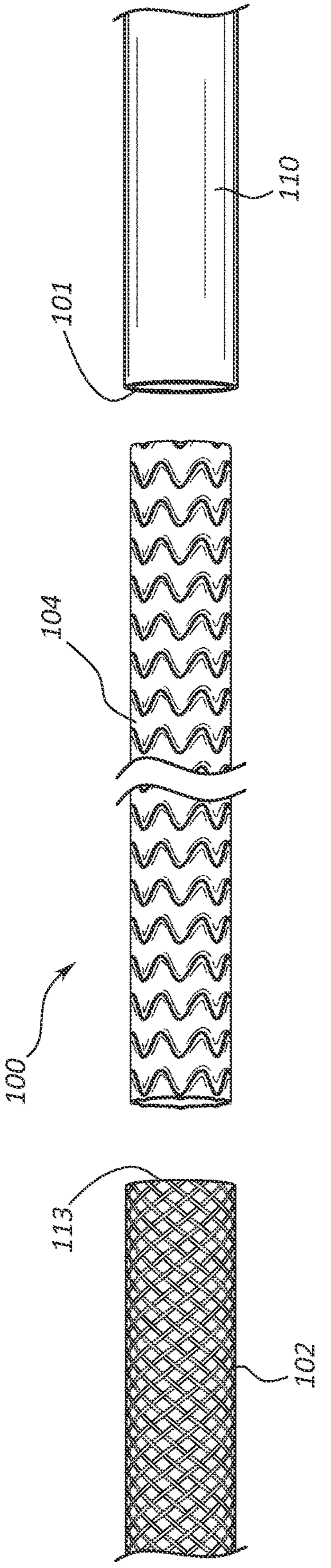
FIG. 1 is a simplified perspective view of certain components of a vascular access system.

In the United States, approximately 400,000 people have end-stage renal disease requiring chronic hemodialysis. Permanent vascular access sites for performing hemodialysis may be formed by creating an arteriovenous (AV) anastomosis whereby a vein is attached to an artery to form a high-flow shunt or fistula. A vein may be directly attached to an artery, but it may take six to eight weeks before the venous section of the fistula has sufficiently healed and matured to provide adequate blood flow for use with hemodialysis. Moreover, a direct anastomosis may not be feasible in all patients due to anatomical considerations.

Other patients may require the use of artificial graft material to provide an access site between the arterial and venous vascular systems. However, AV grafts still require time for the graft material to mature prior to use, so that a temporary access device must be inserted into a patient for hemodialysis access until the AV graft has matured. The use of temporary catheter access exposes the patient to additional risk of bleeding and infection, as well as discomfort. In addition, patency rates of grafts are still not satisfactory, as the overall graft failure rate may be high. Failure of these grafts is usually due to stenosis at the venous end. These failure rates are further increased in higher-risk patients, such as diabetics, in whom the vascular access is most needed. These access failures result in disruption in the routine dialysis schedule and create hospital costs of over $2 billion per year.

To address these problems various vascular access systems and methods have been developed, as in U.S. Pat. No. 8,690,815 to Porter et al., and U.S. Pat. No. 9,278,172 to Herrig. In such vascular access systems and methods it may be advantageous to use multiple conduits to improve anastomosis with the vasculature and extravascular flow properties. When using multiple conduits, such as multiple artificial vascular catheters, that are connected to each other in the body the conduits may not be labeled with outside diameter measurements. Conduits may be labeled according to the inside diameter of the conduit and, as wall thickness and other parameters may vary between conduits of different design or manufacture, the outside diameter may not consistently relate to the stated inside diameter. Further, in some instances a physician may elect to use a more rigid catheter for one section of the artificial extravascular conduit system, and a more pliable graft for a different section of the same system. If the connector does not accommodate the various conduits, there may be a disruption in the laminar flow of fluid, e.g. blood, through the system. If the fluid is blood, turbulent flow could lead to extensive complications, including thrombosis, which may have significant negative impact on patient morbidity and mortality. Furthermore, in many instances the type and construction of a desired conduit may depend on patient anatomy, therapy type, doctor preference, and so forth. Ability connect two conduits using an expandable stent may thus facilitate flexibility before and during procedures by allowing a practitioner to select a conduit according to factors such as those discussed above while maintaining a smooth transition from one conduit to the next via the connecting expandable stent.

In some instances, use of an expandable stent to connect two conduits would eliminate the need for a strain relief component to minimize kinking of a flexible conduit at the interface between the conduits, as the expandable stent would act as an internal strain relief mechanism.

Expandable stents used to connect two conduits may be sized such that the length of the stent is configured to maintain the position the stent was deployed into both conduits, and resist creep or separation of the conduits from each other. In alternative embodiments, the expandable stent may have anchors or barbs to affix the stent after deployment to the inner walls of the conduits, to provide another mechanism to resist creep or separation of the conduits from each other once the vascular access system has been assembled.

The expandable stent may be previously coupled or prefabricated to be attached to one end of either of the two conduits such that deployment of the stent into the other conduit is sufficient to connect the two conduits. Alternatively, the expandable stent may be simultaneously deployed in both conduits to connect the two conduits.

In the following detailed description, reference is made to the accompanying drawings which form a part hereof and, in which are shown by way of illustration, specific embodiments of the disclosure that may be practiced. These embodiments are described in sufficient detail to enable those of ordinary skill in the art to practice the invention, and it is to be understood that other embodiments may be utilized, and that structural, logical, and electrical changes may be made within the scope of the disclosure. From the following descriptions, it should be understood that components of the embodiments as generally described and illustrated in the figures herein could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

In this description, specific implementations are shown and described only as examples and should not be construed as the only way to implement the present disclosure unless specified otherwise herein. It will be readily apparent to one of ordinary skill in the art that the various embodiments of the present disclosure may be practiced with numerous other vascular access solutions. The devices and methods described herein could be useful in a number of environments that employ conduits used or implanted into the body, such as vascular access devices, ventricular assist devices, total artificial hearts, and various types of hemodialysis systems. It would be apparent to one of ordinary skill in the art that the present disclosure may be practiced in any situation that uses at least one conduit, not just fluid or blood conduits. The environments in which the present disclosure may be practiced include short-term applications, e.g. several days to weeks, and longer-term applications, e.g. months to years.

Referring in general to the following description and accompanying drawings, various embodiments of the present disclosure are illustrated to show its structure and method of operation. Common elements of the illustrated embodiments may be designated with similar reference numerals. It should be understood that the figures presented are not meant to be illustrative of actual views of any particular portion of the actual structure or method, but are merely idealized representations employed to more clearly and fully depict the present invention defined by the claims below.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

While the disclosure is susceptible to various modifications and implementation in alternative forms, specific embodiments have been shown by way of non-limiting example in the drawings and have been described in detail herein. However, it should be understood that the disclosure is not intended to be limited to the particular forms disclosed. Rather, the disclosure includes all modifications, equivalents, and alternatives falling within the scope of the disclosure as defined by the following appended claims and their legal equivalents.

The phrases "connected to" and "coupled to" refer to any form of interaction between two or more entities, including mechanical, electrical, magnetic, electromagnetic, fluid, and thermal interaction. Two components may be connected or coupled to each other even though they are not in direct contact with each other. For example, two components may be coupled to each other through an intermediate component.

The directional terms "proximal" and "distal" are used herein to refer to opposite locations on a medical device. The proximal end of the device is defined as the end of the device closest to the practitioner when the device is in use by the practitioner. The distal end is the end opposite the proximal end, along the longitudinal direction of the device, or the end furthest from the practitioner.

Referring in general to the following description and accompanying drawings, various embodiments of the present disclosure are illustrated to show its structure and method of operation. Common elements of the illustrated embodiments may be designated with similar reference numerals. Accordingly, the relevant descriptions of such features apply equally to the features and related components among all the drawings. Any suitable combination of the features, and variations of the same, described with components illustrated in FIG. 1, can be employed with the components of FIG. 2, and vice versa. This pattern of disclosure applies equally to further embodiments depicted in subsequent figures and described hereinafter. It should be understood that the figures presented are not meant to be illustrative of actual views of any particular portion of the actual structure or method, but are merely idealized representations employed to more clearly and fully depict the present invention defined by the claims below.

Vascular access systems may be designed and constructed as a single-piece, integrated device, or a multi-piece device comprising separate components that are later joined together. Some embodiments of multi-piece devices are discussed in U.S. Pat. No. 8,690,815 to Porter et al. The connectors or interfaces where the separate components of a multi-piece device are joined or attached, are potential sources of turbulent flow within in the lumen of the system. Any indentation or protrusion into or out of the lumen may cause a disruption of flow. In embodiments in which the multi-piece device is a vascular access system, this turbulent flow may disrupts the normal laminar flow of blood. Disruption in the laminar flow of blood creates a potential risk for thrombus development or hemolysis. Thus, in some instances, connectors, and the various components of a multi-piece device, are designed to maintain smooth laminar flow between components through the connector, and also resist creep or separation of the joined components. Such a connector system may be used with AV grafts, peripherally inserted central catheters (PICC), implantable infusion catheters with and without fluid reservoirs, implantable infusion pumps, left ventricular assist devices, and any other device configured to provide laminar flow from one end of a multi-piece device to the other end of the multi-piece device. In some embodiments this connector is an expandable stent which is deployed within the lumen of the conduits that make up the multi-piece vascular access system. In addition to joining fluid conduits, the expandable stent may be used to join conduits to other devices such as reservoirs and needle access ports.

Figure 3:
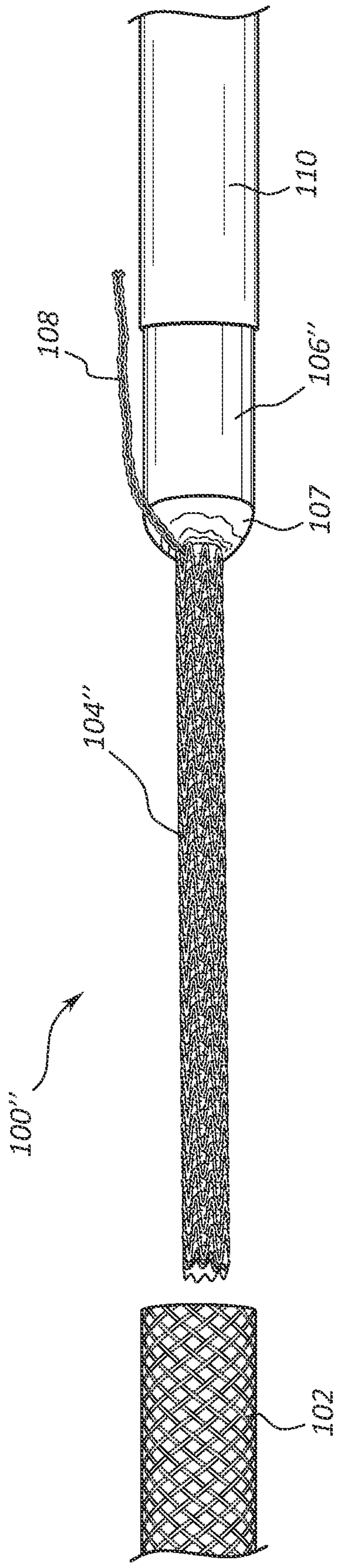
FIG. 3 is a simplified perspective view of certain components of another embodiment of a vascular access system.

FIG. 1 depicts various components of the vascular access system 100. A first conduit 110 with a second end 101 is depicted. An expandable stent 104 is depicted as is a second conduit 102 with a first end 113. The expandable stent 104, may in some embodiments, be used to couple the first conduit 110 to the second conduit 102. In some embodiments the expandable stent 104 can be sized to self-expand within the first and second conduits. In the depicted embodiment of FIG. 1 the expandable stent 104 is coupled to the first conduit 110 before it is coupled to the second conduit 102, in some embodiments the expandable stent 104 may be coupled to the second conduit 102 before it is coupled to the first conduit 110. In some embodiments the first or second conduit may be configured with a stent-like supporting framework. In some embodiments this stent-like frame may extend throughout each conduit, or alternatively may extend for just a portion of either conduit. In some embodiments the expandable stent 104 may exert sufficient radial force to securely couple the first conduit 110 to the second conduit 102, hold the expandable stent in place, and resist separation of the components such that a fluid-tight connection is made while maintaining a continuous lumen throughout. In some embodiments the expandable stent 104 may have barbs or anchors to secure the stent to the inside lumen of the first and second conduits. The expandable stent 104 may be compressed and ready for self-expansion as is depicted in FIG. 3 and discussed further below. The expandable stent 104 may be configured to remain constrained in a compressed configuration until the end user is ready to deploy the stent into one or both of the first and second conduits. The expandable stent 104 in some embodiments may be configured to be deployed using a stent deployment device. As is discussed in greater detail below, the expandable stent 104 in some embodiments may be configured to be deployed simultaneously into both the first and second conduits. In some embodiments the expandable stent 104 may be deployed using a sheath deployment system (not depicted), in which the compressed expandable stent is captured in a deployment sheath, and removal of the sheath allows the stent to expand. In some embodiments the expandable stent 104 may be a balloon expandable stent and may be deployed and expanded using a balloon deployment device. In other embodiments the expandable stent 104 may be configured to couple to a first and second conduit with different inside diameters. In other embodiments the expandable stent 104 may be configured to couple to a first and second conduit with the same inside diameter.

Figure 2:
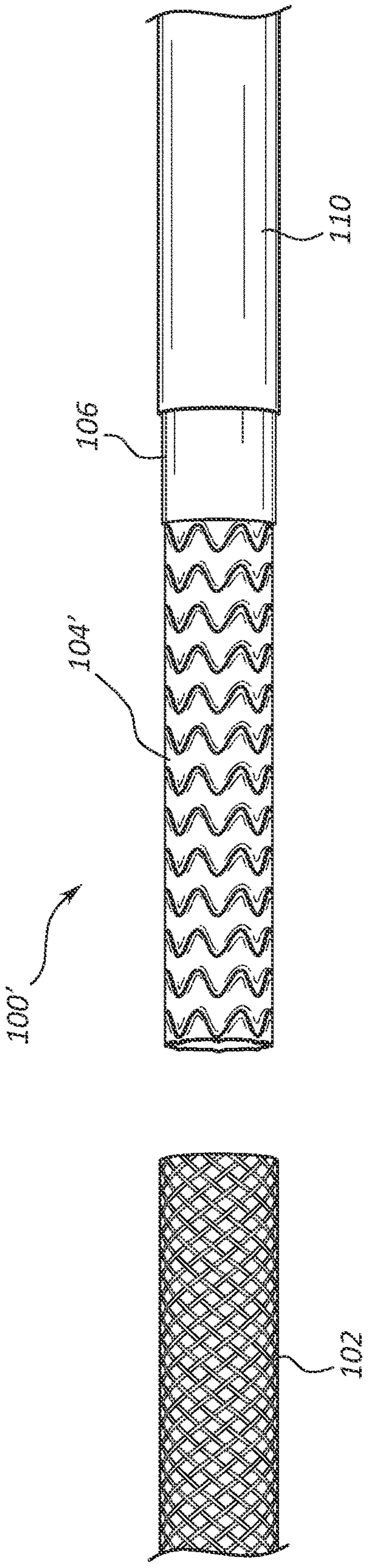
FIG. 2 is a simplified perspective view of certain components of another embodiment of a vascular access system.

FIG. 2 illustrates a vascular access system 100' that can, in certain respects, resemble components of the vascular access system 100 described in connection with FIG. 1. It will be appreciated that all the illustrated embodiments may have analogous features. Accordingly, like features are designated with like reference numerals, with the addition of a prime ' notation following the reference numeral. For instance, the expandable stent is designated as "104" in FIG. 1, and an analogous expandable stent is designated as "104'" in FIG. 2. Relevant disclosure set forth above regarding similarly identified features thus may not be repeated hereafter. Moreover, specific features of the vascular access system and related components shown in FIG. 1 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the vascular access system of FIG. 2. Any suitable combination of the features, and variations of the same, described with respect to the vascular access system 100 and components illustrated in FIG. 1 can be employed with the vascular access system 100' and components of FIG. 2, and vice versa. This pattern of disclosure applies equally to further embodiments depicted in subsequent figures and described hereafter.

FIG. 2 is an alternative embodiment of the vascular access system 100' in which the expandable stent 104' is manufactured to come coupled to the first conduit 110 via an intervening collar 106. In some embodiments the expandable stent 104' is incorporated into first conduit 110 or second conduit 102 through manufacturing processes without a collar such as collar 106. In this alternative embodiment the expandable stent 104' can be deployed in the conduit 102 to which it is not attached, and in so doing couple the conduits 110 and 102 with a fluid-tight bond. In some embodiments the expandable stent 104' can be sized to self-expand within the conduit 102, and exert sufficient radial force against the inside diameter of conduit 102 to securely couple conduits 110 and 102, hold the expandable stent in place, and resist separation of any of the components. The bound components form a fluid-tight continuous lumen running from the first conduit 110 to the second conduit 102. The expandable stent 104' can be similarly compressed and ready for self-expansion as is depicted with reference to stent 104 in FIG. 3. The features discussed herein with reference to expandable stent 104 are also applicable to expandable stent 104'. For example, the expandable stent 104' may be configured to remain constrained in a compressed configuration until the end user is ready to deploy the stent into conduit 102. In some embodiments expandable stent 104' may be a balloon expandable stent and may be deployed and expanded using a balloon deployment device.

FIG. 3 depicts an alternative embodiment of the vascular access system 100" in which the expandable stent 104" is in a compressed state, and a first end 107 of collar 106" is depressed. This embodiment also depicts one possible method of deploying the expandable stent using a pull string 108. The expandable stent 104", may in some embodiments, be used to couple the first conduit 110 to the second conduit 102. In some embodiments the expandable stent 104" can be sized to self-expand within the second conduit 102 by using the deployment string 108. In the illustrated embodiment the pull string 108 is coupled to the collar 106". In some embodiments there may be two pull strings to deploy one end at a time within the first conduit 110 and second conduit 102. In some embodiments the expandable stent 104" may exert sufficient radial force to securely couple the first conduit 110 to the second conduit such that the stent 104" is held in place, and it resists separation of the components creating a fluid-tight connection with a continuous lumen throughout. In some embodiments the expandable stent 104" may have barbs or anchors or other securing structures to secure the stent to the inside lumen of the second conduit 102. FIG. 3 shows the expandable stent 104" in a compressed state ready for deployment into a second conduit 102. The expandable stent 104" may be a balloon expandable stent and may be configured to be deployed and expanded using a balloon deployment device, or other deployment devices.

Figure 4:
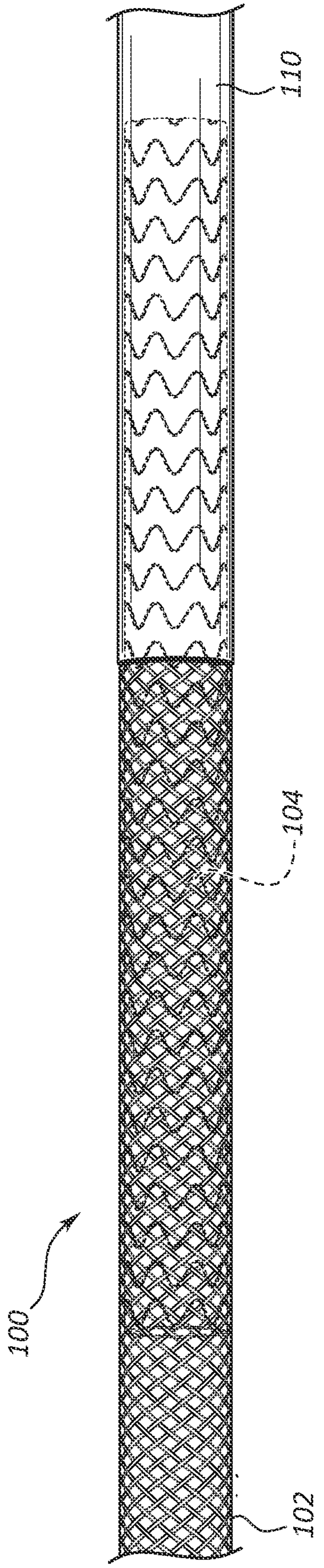
FIG. 4 is a simplified perspective view of a step in connecting components of the vascular access system of FIG. 1.

FIG. 4. Depicts the various components of the vascular access system 100 after the expandable stent 104 has been deployed within both the first conduit 110 and the second conduit 102. This embodiment depicts the expandable stent 104 securely coupling the first conduit 110 to the second conduit 102. In some embodiments this is achieved by the length of the expandable stent being proportionally long enough such that the radial force exerted by the stent alone securely holds the two conduits together forming a fluid-tight continuous lumen. In other embodiments the expandable stent 104 is configured to secure to the lumens of the first conduit 110 and second conduit 102 with barbs, anchors, or other securing devices, which can hold the components together in a fluid-tight state. In some embodiments the expandable stent 104 couples the conduits together while maintaining a low profile within the lumen of the conduits. In these embodiments the expandable stent 104 would reduce the disruption of the laminar flow of fluid passing through the fluid-tight connection. A reduction in disruption of laminar flow would reduce complications of thrombosis formation in the lumen and stenosis of the lumen after implantation. The embodiments depicted in FIGS. 2 and 3 are analogous to those depicted in FIG. 4 which shows the components in the coupled state. Any discussion with reference to FIG. 4 is also applicable to the embodiments discussed with reference to FIGS. 2 and 3.

Figure 5:
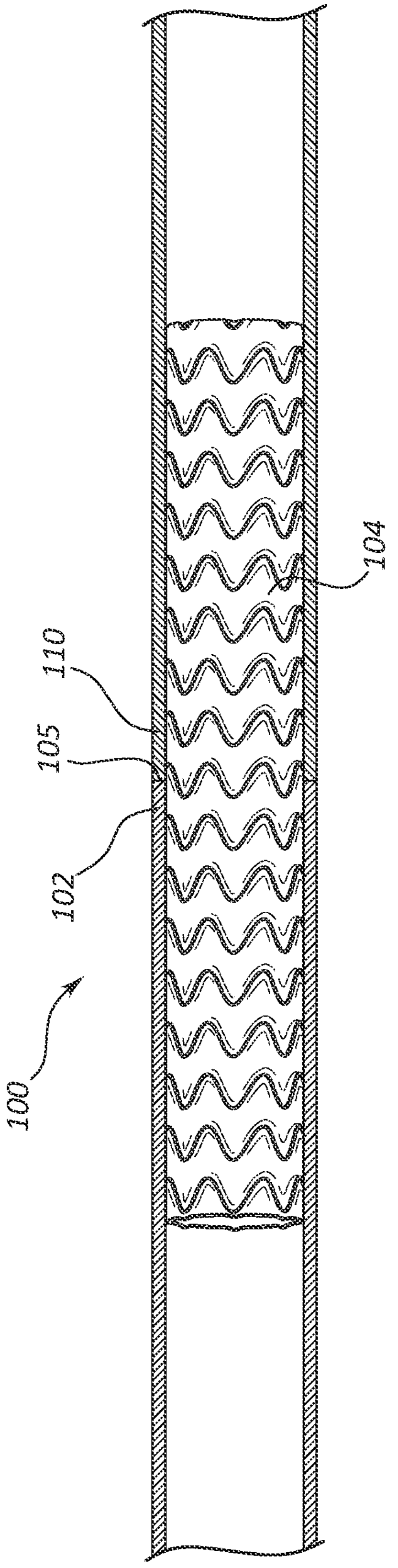
FIG. 5 is a simplified cross-section view of a step in connecting components of the vascular access system of FIG. 1.

FIG. 5 is a cross-section view of FIG. 4 depicted the vascular access system 100 in which the expandable stent 104 has been deployed within a first conduit 110 and a second conduit 102. The stent 104 has formed a fluid-tight seal 105 between the first and second conduits. The embodiments discussed with reference to FIG. 4 are applicable to the cross-section view of FIG. 5.

Figure 6:
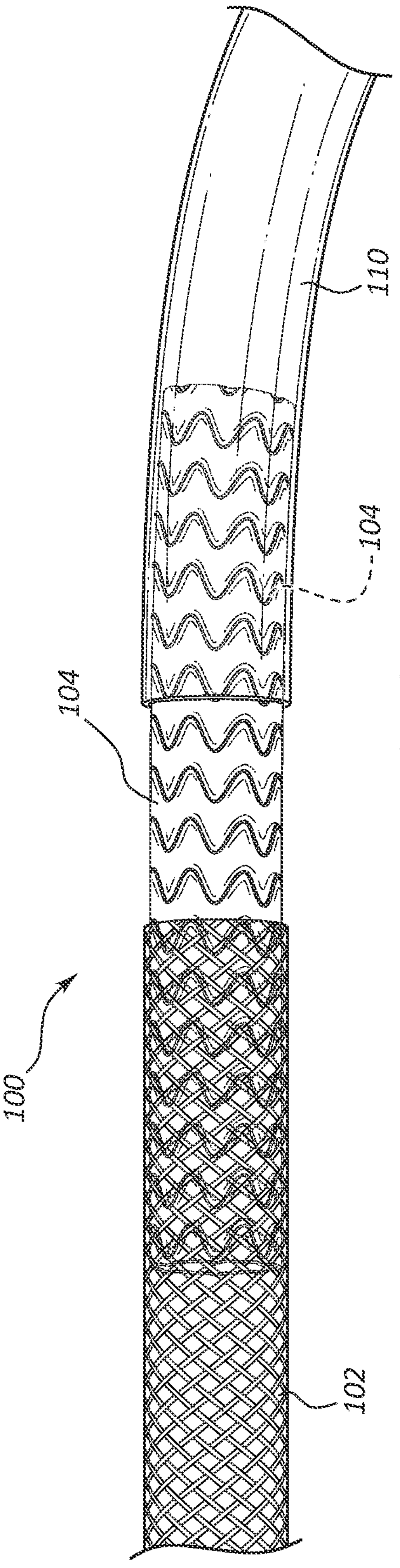
FIG. 6 is a simplified perspective view of a step in connecting components of the vascular access system of FIG. 1.

FIG. 6 is alternative embodiment of the stent 104 deployed inside the first conduit 110 and the second conduit 102. In some embodiments the stent 104 is itself configured to be a fluid-tight conduit. This alternative embodiment depicts a portion of the stent 104 exposed between the first conduit 110 and the second conduit 102. In this embodiment the expandable stent 104 forms a fluid-tight connection with both conduits and is secured within the conduits through the radial force from the deployed stent or by barbs, anchors, or other securing devices coupling the stent securely to the lumens of both the conduits. The end user may choose to leave a portion of the expandable stent 104 exposed between the conduits.

Figure 7A:
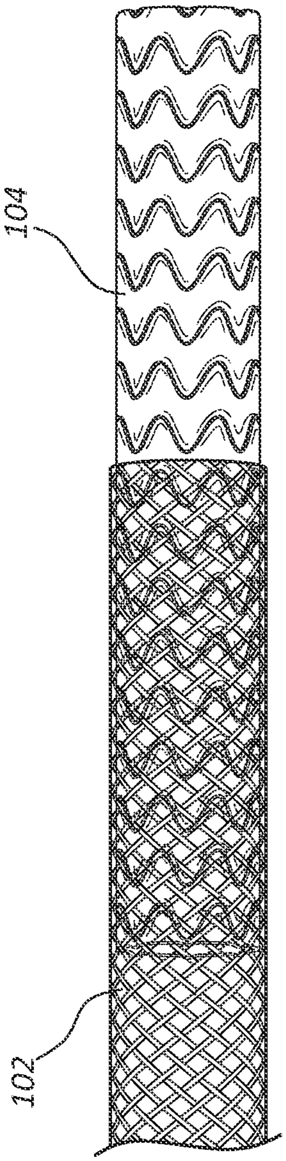
FIG. 7A is a simplified perspective view of a first embodiment of alternative steps in connecting components of a vascular access system.
Figure 7B:
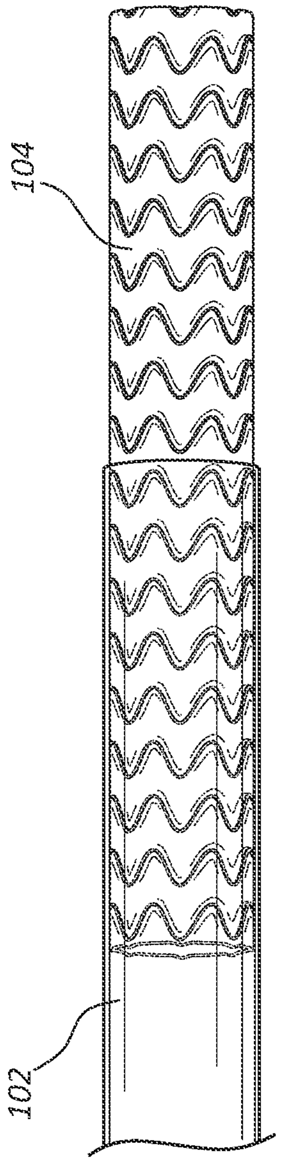
FIG. 7B is a simplified perspective view of a second embodiment of alternative steps in connecting components of a vascular access system.

FIGS. 7A and 7B depict two alternative embodiments in which the expandable stent 104 has been first deployed or pre-manufactured to be coupled to either the first conduit 110 or the second conduit 102.

In some embodiments, the artificial conduits are configured to be accessed for hemodialysis. In other words, during some medical procedures (e.g., hemodialysis), the conduit 102 may be accessed in lieu of the natural vasculature of a patient. In some embodiments, the conduit 102 comprises and/or consists of polytetrafluoroethylene (PTFE), such as expanded PTFE (ePTFE), rotational spun PTFE, or electrospun PTFE. In some embodiments, the conduit 102 and/or 110 comprise silicone. In some embodiments, the conduits 102 and/or 110 comprise a fibrous polymer.

In some embodiments the material layer on the inside diameter of expandable stent 104 may be configured to promote laminar flow through the stent. In addition, in some embodiments the material layer on the inside diameter of expandable stent 104 may match the material of the inside of the first conduit 110, the second conduit 102, or both to promote laminar flow through the vascular access system. In some embodiments the wall thickness of the expandable stent 104 may be thin to create a minimal discontinuity in the flow path. In some embodiments the material layer on the inside diameter of the expandable stent 104 may also be configured to be fluid-tight. In some embodiments in which the expandable stent 104 is pre-coupled to one of the conduits through manufacturing processes, the stent may be configured to be incorporated into the wall of the conduit to reduce or eliminate any discontinuity along the inside surface of the lumen.

In some embodiments, the conduit 102 includes a puncturable and self-sealing wall such that the wall may be punctured by insertion of a needle and then reseal upon withdrawal of the needle. The self-sealing wall may be of any suitable composition. In some embodiments, the self-sealing wall is a multi-layered construct. For example, some embodiments include an outer layer, an inner layer, and at least one tie layer disposed between the outer layer and the inner layer. In some embodiments, one or more of the outer layer and the inner layer comprise PTFE. For example, the outer layer may comprise or consist of expanded PTFE, while the inner layer comprises and/or consists of rotational spun or electrospun PTFE. In some embodiments, the tie layer comprises an elastomer, such as elastomeric silicone. Due, at least in part, to the properties of the silicone, the resulting construct may be self-sealing. In other words, when a needle that has been inserted through the wall is withdrawn from the conduit 102, the wall may seal itself, thereby preventing leakage of blood from the conduit 102.

The expandable stent 104 may be made from any suitable material, such as steel or nitinol. The expandable stent 104 may also include a coat. In some embodiments there are multiple coats. In some embodiments the multiple coats may include a luminal coating or layer and an abluminal coat. In some embodiments the luminal and/or abluminal coat is configured to be continuous with the lumen of one or both of the conduits to minimize or eliminate any discontinuity in the lumen. The coat may be made from any suitable material. For example, in some embodiments, the coat is formed from PTFE, such as fibrous (e.g., electrospun or rotational spun) PTFE. Other polymers may also be used to form the coat of the expandable stent 104. The expandable stent 104 may be configured to transition from a compact state as, in a non-limiting example, shown in FIG. 3 to a deployed state as shown in a non-limiting example in FIG. 4. In some embodiments, the expandable stent 104 is expanded (and thereby deployed) by inflation of a balloon that is positioned within a lumen of the expandable stent 104. In other embodiments, the expandable stent 104 is a self-expanding stent graft that transitions from the compact state to the expanded state when a restraint, such as a sheath or other delivery constraint, is removed from around the expandable stent 104. The restraint may be removed by any suitable manner, such as by retraction of a sheath or by use of a pull string 108 that releases the restraint. For example, a restraint may comprise filaments that extend around a circumference of the expandable stent 104 in a compressed state. These filaments may be coupled to the pull string 108 such that displacement of the pull string 108 decouples the filaments from the expandable stent 104 allowing the expandable stent 104 to expand. The expandable stent 104 may be biased to adopt the expanded state when unconstrained. As described below, the expandable stent 104 may be configured to couple to a conduit such that the expandable stent is in fluid communication with the conduit.

In some embodiments, one or both of the inner surface and the outer surface of any one of the components of the vascular access system 100 may be associated with a therapeutic agent. In other words, the therapeutic agent may be disposed on or embedded within a surface of the vascular access system 100. The therapeutic agent may be released from the surface(s) of the vascular access system 100 to deliver a therapeutically effective dose of the therapeutic agent to the patient when the vascular access system 100 is implanted within a patient. In some embodiments, a first therapeutic agent is associated with the inner surface of the vascular access system 100 and a second therapeutic agent that differs from the first therapeutic agent is associated with the outer surface of the vascular access system 100. In such embodiments, both the first therapeutic agent and the second therapeutic agent may be delivered into the bloodstream of the patient in therapeutically effective doses when the vascular access system 100 is implanted within the patient. In some embodiments, heparin is used as a therapeutic agent. In some embodiments, the therapeutic agent reduces thrombus or tissue proliferation. In some embodiments, one or both therapeutic agents may be delivered to the abluminal tissues to either reduce tissue proliferation and/or enhance tissue incorporation, which may enhance early cannulation of the vascular access system 100.

The vascular access system 100 may be used in any suitable medical procedure, such as to establish vascular access for hemodialysis. For example, where an arteriovenous graft has become occluded or otherwise failed, an alternative artificial flow path that bypasses the occlusion or failure may be established. For example, an artificial flow path may be established from a portion of the arteriovenous graft that is upstream of the occlusion or failure in the arteriovenous graft to the right atrium of the heart.

Figure 8:
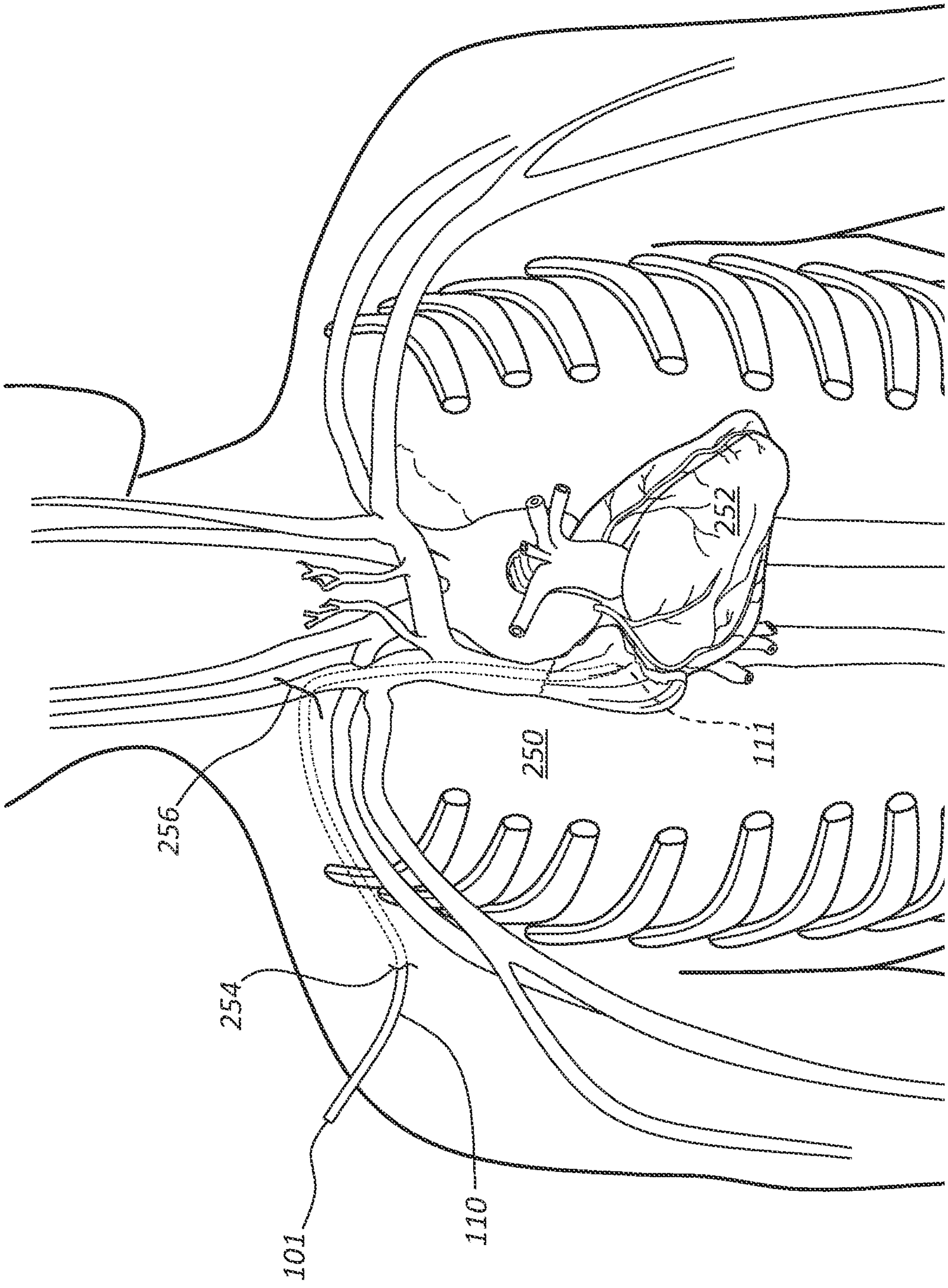
FIG. 8 depicts a portion of one embodiment of the vascular access system of FIGS. 1 and 4.
Figure 9:
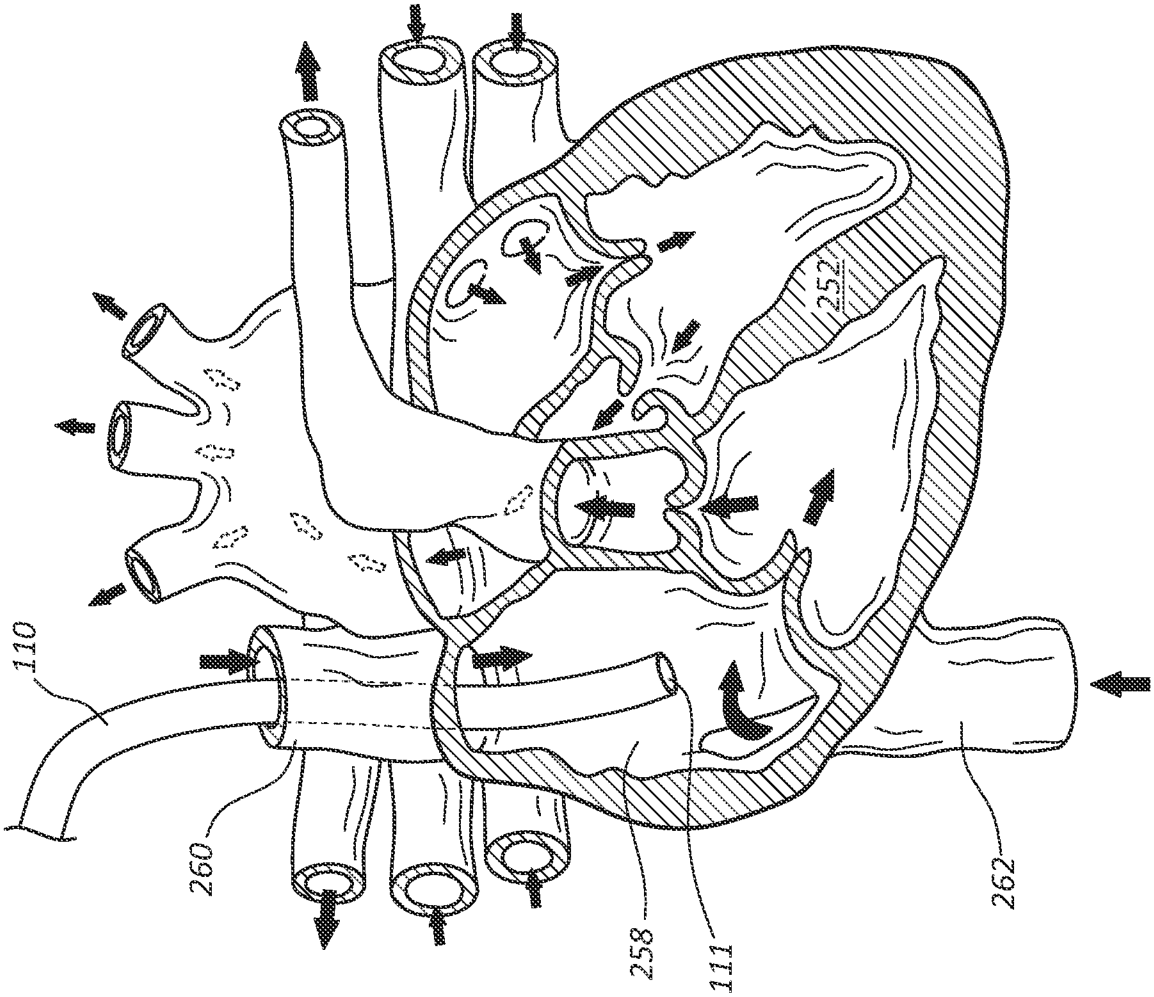
FIG. 9 is a detailed cross-section view of a heart of a patient with one embodiment of the vascular access system.

FIG. 8 depicts one embodiment for the deployment of a first conduit 110 inside the body and vasculature of a patient 250. As shown in FIG. 8, such a medical procedure may initially involve making a first incision 256 in or adjacent to the neck of a patient 250 to access the internal jugular vein of the patient 250. A guidewire (not depicted) may then be passed into the internal jugular vein to the inferior vena cava, followed by a dilator (not depicted) that is passed over the guidewire to facilitate insertion of an introducer. The dilator may then be removed, and the introducer (not depicted) passed over the guidewire into the internal jugular vein of the patient 250. Once the introducer is placed within the internal jugular vein, a first end 111 of the first tubular conduit 110 may be inserted through the introducer and advanced within the patient 250 such that the first end 111 of the first conduit 110 passes through the superior vena cava into the right atrium of a heart 252 as depicted in FIGS. 8 and 9. Advancement of the first conduit 110 into the patient 250 may be done under fluoroscopic guidance.

Figure 10:
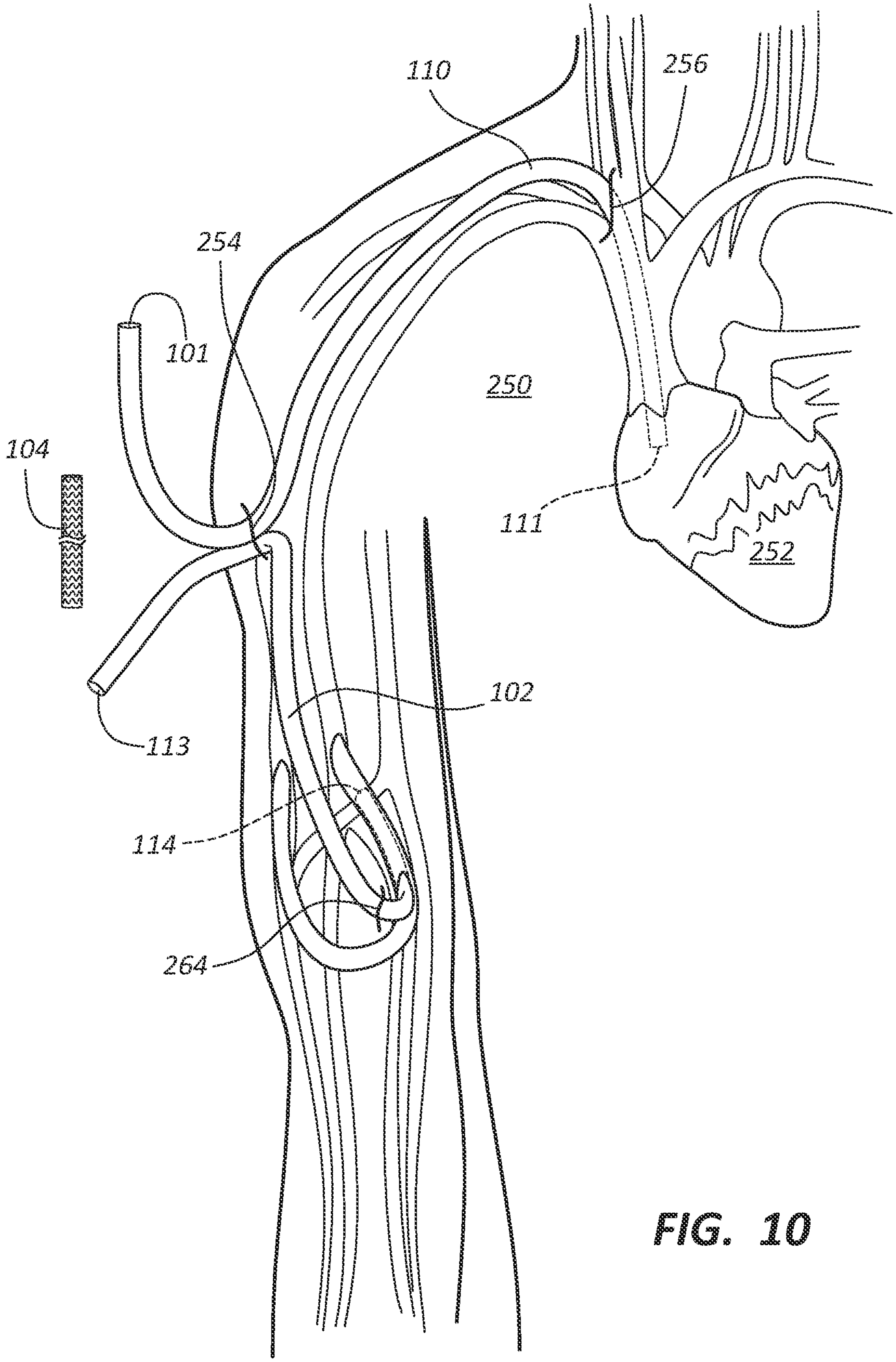
FIG. 10 depicts portions of one embodiment of the vascular access system.

After the first end 111 of the first conduit 110 has been placed within the right atrium of the heart 252, a second incision 254 (see FIG. 10) may be made in the shoulder region of the patient 250 (e.g., adjacent the deltopectoral groove). A tunneling device may then be used to establish a subcutaneous path between the first incision 256 in the neck region of the patient 250 and the second incision 254 in the shoulder region of the patient 250. The second end 101 of the first conduit 110 may then be inserted into the first incision 256 and advanced along the path established by the tunneling device (i.e., the first conduit 110 is tunneled) such that the first conduit 110 extends from the right atrium of the heart 252 to the second incision 254 in the shoulder region of the patient 252 as shown in FIG. 10.

Once the first conduit 110 has been placed such that the first conduit 110 extends from the right atrium of the heart 252 to the second incision 254 in the shoulder region of the patient 250, a third incision 264 (see FIG. 10) may be made in the arm of the patient 250 adjacent the target site of, for example, an arteriovenous graft. For example, the third incision 264 may be made at a position that is upstream of, for example, an occlusion or failure in the arteriovenous graft. The second end 114 of the second tubular conduit 102 may then be coupled to the arteriovenous graft adjacent the third incision 264 in the arm of the patient 250 (see FIGS. 10-13). For example, in some embodiments, the arteriovenous graft may be pierced adjacent the third incision 264 by a needle. A guidewire (not depicted) may then be inserted through the needle and into the arteriovenous graft of the patient 250. In some embodiments the second end 114 of the second conduit 102 is, for example, anastomosed to the arteriovenous graft, or any other vasculature in the arm of the patient 250.

In some embodiments, a distal end of a stent deployment device (not shown) may be inserted into a second end 101 of the first conduit 110 or the first end 113 of the second conduit 102. The practitioner may then manipulate the stent deployment device and expandable stent 104 to deploy the expandable stent 104 in one or both of the first and second conduits. In some embodiments the expandable stent is manufactured to be attached to one end of one of the conduit and the stent deployment device (not shown) may be configured to deploy this affixed expandable stent into the other conduit. For example, a sheath of the stent deployment device may be retracted, thereby allowing a self-expanding stent to deploy within the one or both of the conduits. In some such embodiments, the second conduit 102 may be disposed within a deployment device such that the expandable stent 104 is disposed distal (along the deployment device) from the remaining portion of the second conduit 102, allowing the expandable stent 104 to be advanced by the deployment device into a first conduit 110 before being deployed within a second conduit 102. In other embodiments, a pull string 108 (see FIG. 3) is used to deploy the expandable stent 104 within the one or both of the conduits either one at a time or simultaneously. In still other embodiments, the expandable stent 104 is deployed via a balloon catheter (not depicted).

Figure 13:
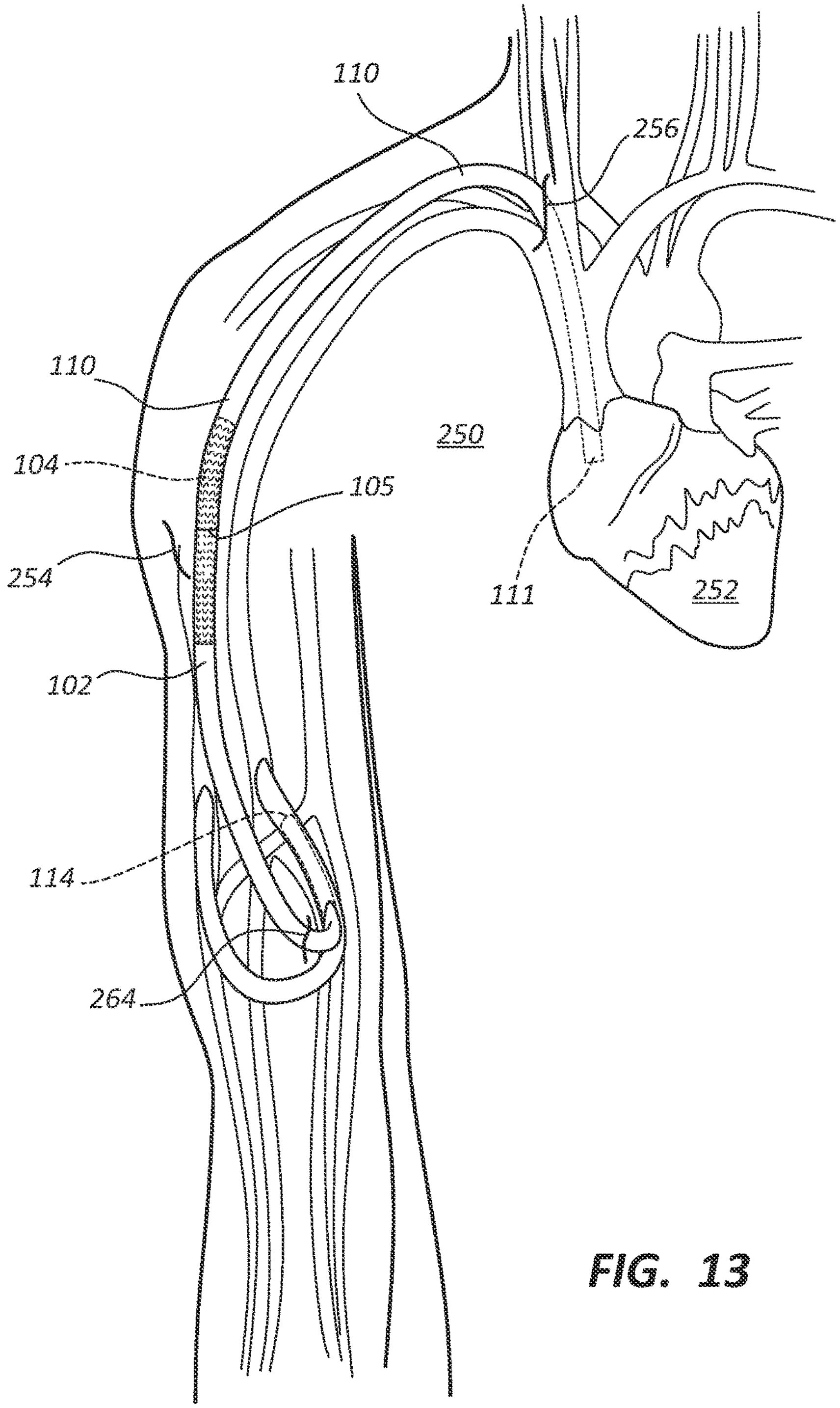
FIG. 13 depicts another embodiment of the vascular access system.

In other words, the expandable stent 104 may be inserted into the one or both of the conduits when in a compact state. Once the expandable stent 104 is appropriately positioned within one or both of the conduits, the expandable stent 104 may be deployed, thereby forming a fluid-tight seal between the conduits as shown in FIGS. 4, 5, and 13. The fluid-tight seal formed by deployment of the expandable stent 104 may divert essentially all of the blood from, for example, the arteriovenous graft through the first and second conduits of the vascular access assembly 100 and into the heart 252 of a patient 250.

A tunneling device (not depicted) may then be used to establish a subcutaneous path between the third incision 264 in the arm of the patient 250 to the second incision 254 in the shoulder region of the patient 250 (see FIG. 10). The second conduit 102 may then be inserted into and advanced through the tunneling device such that the second conduit 102 extends from the third incision 264 to the second incision 254. The tunneling device (not depicted) may then be removed such that the second conduit 102 is disposed within the patient 250 as shown in FIG. 10. In this manner, the tunneling device may facilitate placement and delivery of the second conduit 102 within the patient 250.

With the first end 111 of the first conduit 110 disposed within the right atrium of the heart 252 of the patient 250, the second end of the first conduit 110 may then, if needed, be cut to the appropriate length. In other words, the first conduit 110 may initially (e.g., when manufactured and inserted as described above) have a length that is longer than is needed to establish a flow path from the right atrium of the heart 252 of the patient 250 to the second incision 254 in the shoulder region of the patient 250. The first conduit 110 may then be cut to proper length to facilitate coupling of the second conduit 102 to the first conduit 110 at the second incision 254 in the shoulder region of the patient 250.

Similarly, in some embodiments, the second conduit 102 has an initial length that is longer than is needed to establish a flow path from the second incision 254 in the shoulder region of the patient 250 to the third incision 264 in the arm of the patient 250. In such embodiments, the first end 113 of the second conduit 102 may be cut to the appropriate length once the second conduit 102 has been inserted into the patient 250. In other embodiments, no cutting of the second conduit 102 is needed. In still other embodiments, the expandable stent 104 is manufactured coupled to the second conduit 102.

Once the first conduit 110 and the second conduit 102 are the proper length, the second conduit 102 may be coupled to the first conduit 110. The expandable stent 104 may either be deployed in one of the two conduits followed by deployment into the second conduit, or the expandable stent graft may be simultaneously deployed within each conduit. In some embodiments, one of the conduits will not be cut down as it will have the expandable stent manufactured to be coupled to the conduit. In this embodiment the expandable stent 104 will then be deployed into the other conduit in such a way as to engage the inner wall with the conduit it is deployed within. Such engagement may establish a fluid-tight connection between the first conduit 110 and the second conduit 102. Establishment of a fluid-tight connection can be confirmed by attaching the second end of the second conduit 102 to a syringe and advancing fluid (e.g., heparinized saline) through the system.

Once a flow path from, for example, the arteriovenous graft to the heart 252 has been established as shown in FIG. 13, the first incision 256, the second incision 254, and the third incision 264 may be closed via any suitable technique. In this manner, the vascular access system 100 may, when implanted and assembled, be a fully subcutaneous surgical implant. The implanted and assembled vascular access system 100 may also, as described above, be implanted without establishing a venous anastomosis.

The implanted vascular access system 100 may be used to facilitate vascular access. For example, in the case of hemodialysis, a practitioner may insert a first needle through the skin of the patient 250 and into the vascular access system 100. More particularly, the first needle may be inserted into the second conduit 102. Fluid may be withdrawn from the vascular access system 100 and drawn into a dialysis machine that purifies the blood. The purified blood may then be returned to the patient 250 via a second needle that extends through the skin of the patient 250 and into more central location of the second conduit 102.

The steps of the procedure described above are only exemplary in nature. In other words, the vascular access system 100 may be implanted into the patient 250 via a procedure that deviates somewhat from the procedure described above. One of ordinary skill in the art, having the benefit of this disclosure, will also appreciate that some of the steps described above need not be performed in the precise order that is specified above. In addition, any of the exemplary procedure described above can be performed with any one of the various embodiments described herein.

Figure 11:
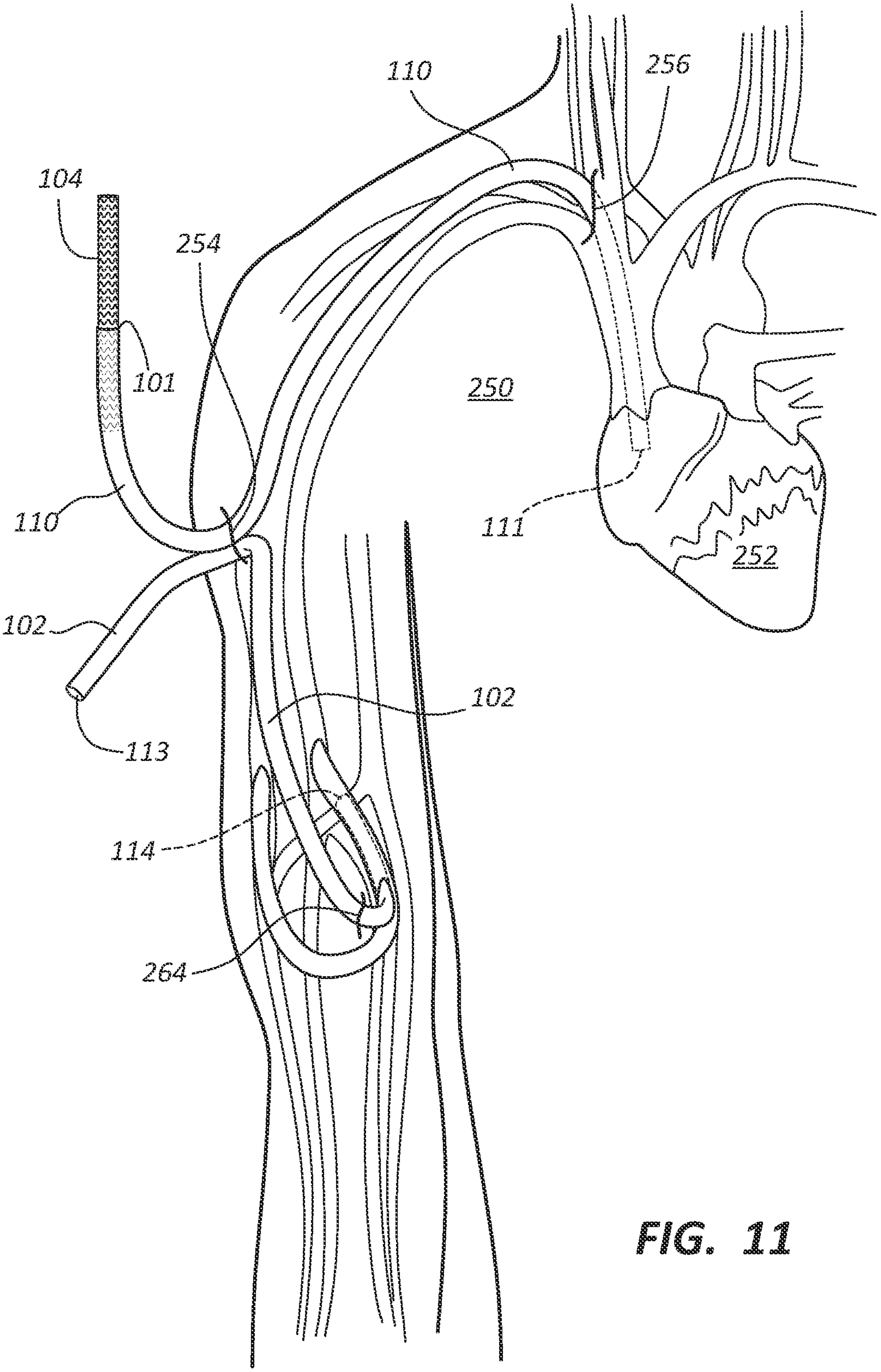
FIG. 11 depicts portions of one embodiment of the vascular access system.

FIG. 11 depicts a first conduit 110 and an expandable stent 104 that is coupled to the second end 101 of the first conduit 110, as is depicted in FIGS. 7A and/or 7B. The expandable stent 104 may then be made ready to couple to the first end 113 of the second conduit 102. In some embodiments a second pull string (not shown) may be configured to compress part of the expandable stent 104 to then be deployed in the second conduit 102. In some embodiments the expandable stent is first deployed in the second conduit 102 followed by deployment in the first conduit 110.

Figure 12:
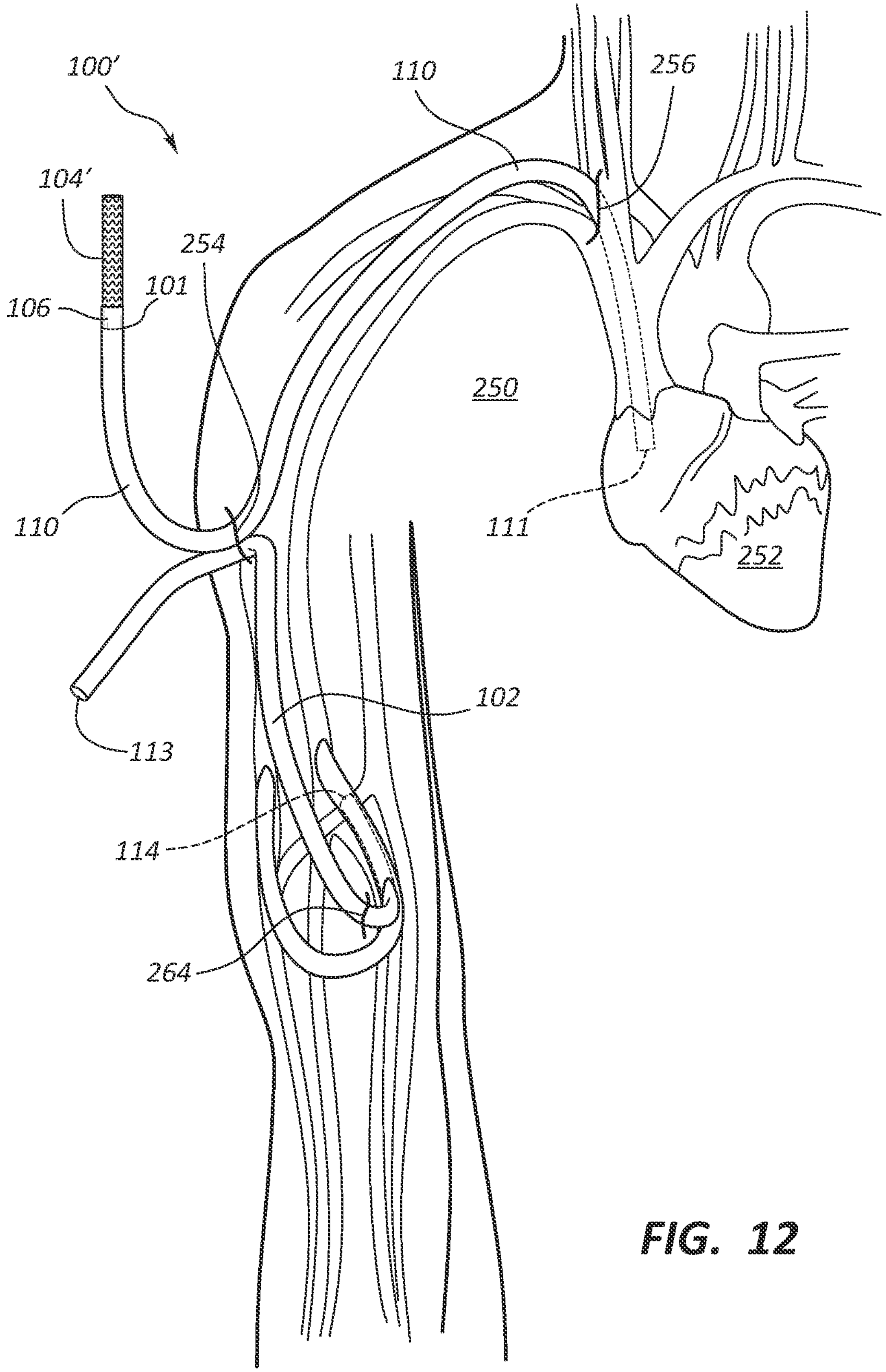
FIG. 12 depicts an alternate embodiment of the vascular access system.

FIG. 12 depicts another embodiment in which the expandable stent 104' is manufactured to be coupled to the first conduit 110. In the depicted embodiment, the vascular access system 100' includes a collar 106 that is disposed around a periphery of the expandable stent 104. In some embodiments the expandable stent 104' is incorporated into the first conduit 110 or second conduit 102 through manufacturing process without a collar such as collar 106. In some embodiments the expandable stent 104' may be compressed with a pull string (not shown) or other means, to prepare the stent for deployment into the second conduit 102. In some embodiments the expandable stent 104' is coupled first to the second conduit 102 with a collar 106 disposed around a periphery of the stent. In this embodiment the stent 104' would then be compressed and made ready to deploy in the first conduit 110.

In some embodiments, the collar 104 is configured to transition between a compact state (FIG. 3) in which the collar 106 adopts a low-profile configuration to a deployed state (FIG. 2) in which the collar 106 extends outward from the exterior surface of the expandable stent 104. When the expandable stent 104 is initially inserted into a second conduit 102, the collar 106 may be in a compact state as shown in FIG. 3. Once the expandable stent 104 has been inserted into the second conduit 102, the collar 106 may transition to the deployed state as shown in FIG. 2. In some embodiments, this transition occurs as the expandable stent 104 is deployed. In some instances, the collar 106 may be deployed before the entire expandable stent 104 to facilitate positioning of the expandable stent 104. For example, an expanded collar 106 may be brought into contact with a wall of the conduit, before the entire expandable stent 104 is expanded and is thus more easily displaceable. The collar 106 may be any suitable shape. For example, in the depicted embodiment, the collar 106 is a relatively thin, ring-shaped sheet of material.

In some embodiments, the collar 106, when unconstrained, is angled relative to the expandable stent 104. For example, the collar 106 may form an acute angle (θ) with the expandable stent 104. In some embodiments, the acute angle θ is between 15° and 75°, between 30° and 60°, and/or between 35° and 55°. The angle relationship between the collar 106 and the expandable stent 104 may facilitate positioning of the collar 106 to function as a seal. For example, as shown in FIG. 13, the deployed collar 106 may function as a seal, thereby preventing or reducing the leakage of blood from the coupled first and second conduits. The collar 106 may also prevent or reduce the risk of withdrawal of the expandable stent 104 from one or both conduits. Stated differently, the collar 106 may serve as a stop that prevents withdrawal of the expandable stent 104 from the conduits it is deployed within. FIG. 13 further depicts an embodiment of any one of the various vascular access systems, and procedures for implantation into a patient. The stent 104 is deployed inside the lumen of both the first conduit 110 and the second conduit 102 and has formed a fluid-tight seal between all the components of the vascular access system, and provides a continuous lumen from the arm of a patient to the heart 252.

During placement and/or implantation of vascular access system, such as those describe above, various strategies may be employed to reduce or prevent the loss of blood. For example, in some embodiments, various clamps are used during implantation to restrict fluid flow through a portion of the first conduit and/or the second conduit. In other or further embodiments, the first conduit and/or the second conduit include one of more valves that obstruct fluid flow, thereby preventing the loss of blood during implantation. For example, in some embodiments, a valve is disposed adjacent the second end of the first conduit or the first end of the second conduit. The valve may be configured to transition from a first configuration that prevents fluid flow through the valve when the first conduit and the second conduit are uncoupled from each other to a second configuration that allows fluid flow through the valve when the first conduit and the second conduit are coupled to each other. In some embodiments, fluid flow is restricted by a balloon that is disposed within a portion of the vascular access assembly.

Kits that include a vascular access assembly are also within the scope of this disclosure. For example, a kit may include any of the vascular access system described above. The kit may also include other elements, such as instructions for using the vascular access system to establish a flow path from an artery or an arteriovenous graft of a patient to a heart of the patient. Kits may additionally or alternatively include (1) one or more clamps for preventing fluid flow through a portion of a tubular conduit, (2) scissors, (3) plugs for preventing fluid flow through an end of a tubular conduit, (4) a tunneling device, (5) a syringe, (6) one or more guidewires, (7) gauze pads, (8) contrast fluid, and/or (9) saline (e.g., heparinized saline), among other potential elements.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

While the disclosure is susceptible to various modifications and implementation in alternative forms, specific embodiments have been shown by way of non-limiting example in the drawings and have been described in detail herein. However, it should be understood that the invention is not intended to be limited to the particular forms disclosed. Rather, the invention includes all modifications, equivalents, and alternatives falling within the scope of the invention as defined by the following appended claims and their legal equivalents.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art, and having the benefit of this disclosure, that changes may be made to the details of the above-described embodiments without departing from the underlying principles of the disclosure herein.

We claim:

1. A vascular access system, comprising:

a first conduit extending between a first end and a second end, the first end configured to be disposed within the vena cava of a patient; and a second conduit extending between a first end and a second end, the second conduit configured to be anastomosed directly to the vasculature of the patient;

wherein the second end of the first conduit comprises an expandable stent configured to be deployed within the second conduit by radial expansion to exert force against an inner wall of the second conduit, and wherein the expandable stent comprises a fluid tight conduit with a portion beyond the second conduit exposed to the subcutis.

2. The vascular access system of claim 1, wherein the expandable stent comprises a self-expanding stent.

3. The vascular access system of claim 1, wherein the expandable stent comprises a balloon expandable stent.

4. The vascular access system of claim 1, wherein the first conduit or the second conduit comprises a fibrous polymer.

5. The vascular access system of claim 1, wherein one or both of the first conduit and the second conduit comprise a puncturable and self-sealing wall material such that the wall material may be punctured by insertion of a needle and then reseal upon withdrawal of the needle.

6. The vascular access system of claim 1, wherein the vascular access system, when implanted and assembled, is a fully subcutaneous implant.

7. The vascular access system of claim 1, wherein the length of the expandable stent is sufficient to maintain the position of the expandable stent when deployed in the second conduit.

8. The vascular access system of claim 1, wherein the expandable stent is formed with the first conduit during the manufacturing process.

9. The vascular access system of claim 1, wherein the expandable stent is coupled to the first conduit by a practitioner during use.

10. The vascular access system of claim 1, wherein the expandable stent is integrally coupled to the first conduit.

11. The vascular access system of claim 1, wherein the assembled vascular access system resists kinking and pinching of the first conduit and/or the second conduit.

12. A method for implanting a vascular access system, the method comprising:

coupling a graft portion of an access system to the vasculature in the arm of a patient;

inserting a first end of a reinforced portion of the access system into a vena cava of the patient and positioning a segment of the reinforced portion outside the vasculature of the patient and along the subcutaneous path; and expanding a second end of the reinforced portion radially against an inner wall of an end of the graft portion to couple the reinforced portion to the graft portion in a lumen;

wherein the second end introduces no discontinuity along an inside surface of the lumen.

13. The method of claim 12, wherein the reinforced portion comprises a self expanding stent and wherein expanding the second end of the of the reinforced portion comprises deploying the self expanding stent in the graft portion.

14. The method of claim 12, wherein expanding the second end of the reinforced portion comprises inflating a balloon to expand the stent.

15. The method of claim 12, wherein the graft portion and the reinforced portion are positioned to form a continuous lumen.

16. The method of claim 12, further comprising subcutaneously tunneling a portion of the graft portion.

17. A method for implanting a vascular access system, the method comprising:

inserting a first conduit into a patient such that a first end of the first conduit is positioned within the vena cava of a patient, a second end of the first conduit comprising an expandable stent;

inserting a second conduit into the patient such that the second conduit extends from an anastomosis in an arm of the patient to the first conduit; and deploying the expandable stent by radial expansion to couple the expandable stent to an inner wall of the second conduit, such that there is a continuous lumen from the first conduit to the second conduit and such that a portion of the expandable stent is disposed outside the first conduit, the second conduit, and the vasculature of the patient.

18. The method of claim 17, wherein the first conduit comprises a self expanding stent and wherein deploying the expandable stent comprises allowing the self expanding stent to expand.

19. The method of claim 17, wherein deploying the expandable stent comprises inflating a balloon to expand the stent.

20. The method of claim 17, wherein the first conduit and the second conduit are positioned to form a continuous lumen.

* * * * *